(12) United States Patent
Yano et al.

(10) Patent No.: US 11,458,229 B2
(45) Date of Patent: Oct. 4, 2022

(54) VISCOELASTIC COMPOSITION

(71) Applicants: Jichi Medical University, Tokyo (JP); Otsuka Pharmaceutical Factory, Inc., Tokushima (JP)

(72) Inventors: Tomonori Yano, Tochigi (JP); Atsushi Ohhata, Tokushima (JP); Toshihiro Goto, Tokushima (JP); Yuji Hiraki, Tokushima (JP)

(73) Assignees: OTSUKA PHARMACEUTICAL FACTORY, INC., Tokushima (JP); JICHI MEDICAL UNIVERSITY, Tokyo (JP)

(*) Notice: Subject to any disclaimer, the term of this patent is extended or adjusted under 35 U.S.C. 154(b) by 477 days.

(21) Appl. No.: 15/764,243

(22) PCT Filed: Sep. 28, 2016

(86) PCT No.: PCT/JP2016/078704
§ 371 (c)(1),
(2) Date: Mar. 28, 2018

(87) PCT Pub. No.: WO2017/057504
PCT Pub. Date: Apr. 6, 2017

(65) Prior Publication Data
US 2018/0280587 A1    Oct. 4, 2018

(30) Foreign Application Priority Data
Sep. 30, 2015    (JP) .............................. JP2015-195105

(51) Int. Cl.
*A61L 31/04*    (2006.01)
*A61L 31/14*    (2006.01)
(Continued)

(52) U.S. Cl.
CPC ............. *A61L 31/042* (2013.01); *A61B 1/015* (2013.01); *A61L 31/028* (2013.01); *A61L 31/041* (2013.01); *A61L 31/14* (2013.01); *A61L 31/145* (2013.01)

(58) Field of Classification Search
CPC .......... A61B 1/012; A61B 1/015; A61B 1/12; A61B 1/126; A61B 1/00091
See application file for complete search history.

(56) References Cited

U.S. PATENT DOCUMENTS 6,031,017 A * 2/2000 Waki ....................... A61L 15/28
                                                          522/84
6,113,594 A    9/2000 Savage
(Continued)

FOREIGN PATENT DOCUMENTS

CN    1207744    2/1999
CN    1098863 C    1/2003
(Continued)

OTHER PUBLICATIONS

Office Action for corresponding Philippines Patent Application No. 1/2018/500646 dated Feb. 29, 2000.
(Continued)

*Primary Examiner* — Alexandra L Newton
(74) *Attorney, Agent, or Firm* — Wood, Phillips, Katz, Clark & Mortimer

(57) ABSTRACT

The purpose of the present invention is to provide a viscoelastic composition having excellent operability, which is suitable for use in securing the field of view of an endoscope when opaque dark-colored liquid accumulates inside a canal and obstructs the field of view of the endoscope, the viscoelastic composition securing the field of view by pushing the liquid aside, and to provide a method for securing the field of view of an endoscope using the viscoelastic composition. The viscoelastic composition for securing the field
(Continued)

VISCOUS COMPOSITION A (BEFORE INJECTION)

VISCOUS COMPOSITION A (AFTER INJECTION)

of view of an endoscope comprises a substance having viscoelastic properties and water, preferably has a hardness of 550 N/m$^2$ or less, a viscosity (25° C.) of 200 to 2,000 mPa·s, and a loss tangent of 0.6 or less, and more preferably has an electrical conductivity of 250 μS/cm or less. The method for securing the field of view of an endoscope comprises feeding the viscoelastic composition from a proximal part of the endoscope, through a channel, into a distal part of the endoscope.

12 Claims, 13 Drawing Sheets

(51) Int. Cl.
  *A61B 1/015* (2006.01)
  *A61L 31/02* (2006.01)

(56) References Cited

U.S. PATENT DOCUMENTS

| | | | |
|---|---|---|---|
| 2005/0049459 | A1 | 3/2005 | Hern |
| 2006/0040894 | A1 | 2/2006 | Hunter et al. |
| 2009/0062233 | A1 | 3/2009 | Ji |
| 2009/0186094 | A1 | 7/2009 | Vogel et al. |
| 2011/0054326 | A1* | 3/2011 | Barnett ............... A61B 1/126 600/453 |
| 2012/0209074 | A1 | 8/2012 | Titus |
| 2013/0045182 | A1 | 2/2013 | Gong |
| 2015/0065795 | A1 | 3/2015 | Titus |
| 2016/0130458 | A1* | 5/2016 | Herbots ............... B05D 1/02 428/412 |
| 2017/0042408 | A1* | 2/2017 | Washburn ............ A61B 1/07 |

FOREIGN PATENT DOCUMENTS

| | | |
|---|---|---|
| CN | 101039683 A | 9/2007 |
| CN | 103429138 A | 12/2013 |
| JP | 2000-513970 A | 10/2000 |
| JP | 2007-506463 A | 3/2007 |
| JP | 2011-509932 A | 3/2011 |
| JP | 2013-510175 A | 3/2013 |
| WO | 2014/197749 A1 | 12/2014 |

OTHER PUBLICATIONS

Office Action for corresponding Australian Application No. 2016329572 dated Nov. 29, 2019.
Office Action for corresponding Brazilian Application No. BR 112018005842-4 dated Oct. 29, 2019.
Office Action for corresponding Taiwanese Application No. 105131779 dated Feb. 20, 2020.
Office Action for corresponding Egyptian Patent Application No. 2018030519 dated Aug. 12, 2020.
Office Action for corresponding Indonesian Patent Application No. 1/2018/500646 dated Jul. 23, 2020.
Supplementary European Search Report for corresponding European Application No. EP 16 85 1675 dated May 3, 2019.
Office Action for corresponding Chinese Patent Application No. 201680056961.1 dated Dec. 29, 2020.
Office Action for corresponding Korean Patent Application No. 10-2018-7010921 dated Jan. 21, 2021.
Office Action for corresponding Canadian Patent Application No. 3000614 dated Feb. 21, 2021.
Office Action for corresponding Canadian Patent Application No. 3000614 dated Sep. 3, 2021.
Office Action for corresponding Korean Patent Application No. 10-2018-7010921 dated May 27, 2021.
Office Action for corresponding Korean Patent Application No. 20211012 dated Oct. 12, 2021.
Office Action for corresponding Indian Patent Application No. 201847015259 dated Jun. 18, 2021.
Extended European Search Report for EP Application No. 20216871.2 dated Apr. 23, 2021.
Chinese Office Action for corresponding Application No. 201680056961.1 dated Dec. 6, 2021.
Office Action for corresponding Korean Patent Application No. 10-2018-7010921 dated Oct. 12, 2021.
Written Opinion for the corresponding PCT application No. PCT/JP2016/078704 (Box 5).
International Search Report for corresponding PCT application No. PCT/JP2016/078704.
International Preliminary Report on Patentability for the corresponding PCT application No. PCT/JP2016/078704.
Naishikyo, K et al., S4-06 Gel immersion endoscopy (2015) 87, Supplement, s85, ISSN2187-4999.
Yano et al., 885 Gel immersion Endoscopy: a Novel Method Using Gel to Secure the Visual Field During Endoscopy, Gastrointestinal Endoscopy, (2015) 81, No. 5, Supplement, AB177, ISSN1097-6779.
Office Action for corresponding Chinese Application No. 201680056961.1 dated May 21, 2020.
Office Action for corresponding Korean Patent Application No. 10-2018-7010921 dated Jul. 29, 2021.
Hironori Yamamoto et al., "Colonoscopy in flowing water for lower GI bleeding: a reliable method for confirmation of bleeding points for endoscopic treatment", Gastrointestinal Endoscopy, vol. 52(5), pp. 678-681, 2000.
Office Action for corresponding Chinese Application No. CN201680056961.1 dated Jul. 30, 2021.
Office Action for corresponding Chinese Patent Application No. 201680056961.1 dated May 9, 2022.

\* cited by examiner

VISCOUS COMPOSITION A (BEFORE INJECTION)

VISCOUS COMPOSITION A (AFTER INJECTION)

VISCOUS COMPOSITION B (BEFORE INJECTION)

VISCOUS COMPOSITION B (AFTER INJECTION)

VISCOELASTIC COMPOSITION

TECHNICAL FIELD

The present invention relates to a viscoelastic composition suitable for use in securing the field of view of an endoscope, and a method for securing the field of view of an endoscope using the viscoelastic composition. More particularly, the invention relates to the viscoelastic composition having excellent operability, which is suitable for use in securing the field of view of an endoscope when opaque dark-colored liquid accumulates inside a canal and obstructs the field of view of the endoscope, the viscoelastic composition securing the field of view by pushing the liquid aside, and also relates to a method for securing the field of view of an endoscope using the viscoelastic composition.

BACKGROUND ART

Endoscopes may be used to observe the interior of a fine canal such as an alimentary canal or a bile duct. However, if dark-colored liquid that would block light, such as blood, intestinal juice or bile, or a semi-solid material such as food residue or excrement accumulates in the interior of a canal, the field of view of an endoscope is obstructed, and the interior state of the canal cannot be fully observed. In these circumstances, the field of view of an endoscope has been hitherto secured by conveying water or gas into the interior of the canal. Conveying water means a method of injecting water such as tap water into the canal and washing away the liquid or the semi-solid material inside the canal. The field of view is temporarily secured in the method by removing the liquid or the semi-solid material inside the canal; however, in many cases, the liquid or the semi-solid material thus removed is mixed with tap water or the like, opaque liquid thus suspended diffuses in the canal, and securing the field of view is still difficult. On the other hand, conveying gas means a method of blowing air into the interior of the canal thereby removing the liquid or the semi-solid material in the canal. The field of view is also temporarily secured in the method by removing the liquid or the semi-solid material inside the canal; however, when there is a hemorrhage site, removing blood is difficult, and the field of view is not secured. Therefore, there have been problems associated with difficulties in identifying a hemorrhage site and operating for a hemostasis treatment. Therefore, there has been an urgent necessity in developing a method for securing the field of view of an endoscope with excellent operability.

Patent Literature 1 discloses a method of treating urinary incontinence, rectal incontinence, vesicoureteral reflux, or the like by injecting a hydrogel consisting of crosslinked polymers into the urethra or the rectum.

Patent Literature 2 discloses a hydrogel composition comprising a polysaccharide, synthetic polymer, and cross-linking agent. It seems that this hydrogel composition is crosslinked and cured with a buffer solution and becomes a sticky hydrogel.

Patent Literature 3 discloses a method of inflating a body cavity such as the uterus by filling the body cavity with a physiological fluid such as physiological saline or lactated Ringer's solution so as to treat the interior of the body cavity.

CITATION LIST

Patent Literatures

Patent Literature 1: JP 2007-506463 A
Patent Literature 2: JP 2013-510175 A
Patent Literature 3: JP 2000-513970 A

SUMMARY OF INVENTION

Technical Problem

The problem of the present invention is to provide a viscoelastic composition having excellent operability, which is suitable for use in securing the field of view of an endoscope when opaque dark-colored liquid accumulates inside a canal and obstructs the field of view of the endoscope, the viscoelastic composition securing the field of view by pushing the liquid aside, and to provide a method for securing the field of view of an endoscope using the viscoelastic composition. The problem desirably includes providing the viscoelastic composition that makes it possible to assist a simplified hemostasis treatment.

Solution to Problem

The inventors of the present invention conducted intensive studies in order to solve the aforementioned problems, and as a result, the inventors found that the use of a viscoelastic composition having elasticity together with viscosity is useful, and that particularly by defining the following physical properties: hardness, viscosity, and loss tangent, the composition exhibits excellent operability when used with an endoscope with securing the satisfactory field of view. Thus, the inventors finally completed the present invention as described below. Further, the inventors also found that by adjusting the electrical conductivity of the viscoelastic composition, assistance of a simplified hemostasis treatment is possible with securing the satisfactory field of view.

(1) A viscoelastic composition for securing the field of view of an endoscope, the viscoelastic composition comprising a thickening substance and water.

(2) The viscoelastic composition according to (1), wherein the viscoelastic composition has a hardness of 550 N/m$^2$ or less, a viscosity at 25° C. of 200 to 2,000 mPa·s, and a loss tangent of 0.6 or less.

(3) The viscoelastic composition according to (2), wherein the viscoelastic composition further has an electrical conductivity of 250 µS/cm or less.

(4) A method for securing the field of view of an endoscope, the method comprising feeding the viscoelastic composition according to any one of (1) to (3) from a proximal part of the endoscope, through a channel, into a distal part of the endoscope.

(5) The method according to (4), wherein the endoscope is a medical endoscope.

Advantageous Effects of Invention

The viscoelastic composition of the present invention is both viscous and elastic, and due to the viscoelasticity, the viscoelastic composition is capable of physically pushing aside liquid such as blood, intestinal juice or bile, or a semi-solid material such as food residue or excrement. Further, since the viscoelastic composition of the present invention does not easily mix with the aforementioned liquid or semi-solid material, suspension does not occur. Furthermore, since the viscoelastic composition of the present invention has adequate consistency, diffusion does not occur thereby making it possible to secure a satisfactory field of view. Moreover, the viscoelastic composition of the present invention may have a reduced electrical conductivity by including no material having electrical charge or by including a minimal amount of the material, thereby making it possible to assist hemostasis treatments by means of electroscission, electrocoagulation, etc., while securing the field of view in the presence of the viscoelastic composition.

DESCRIPTION OF EMBODIMENTS

Figure 1:
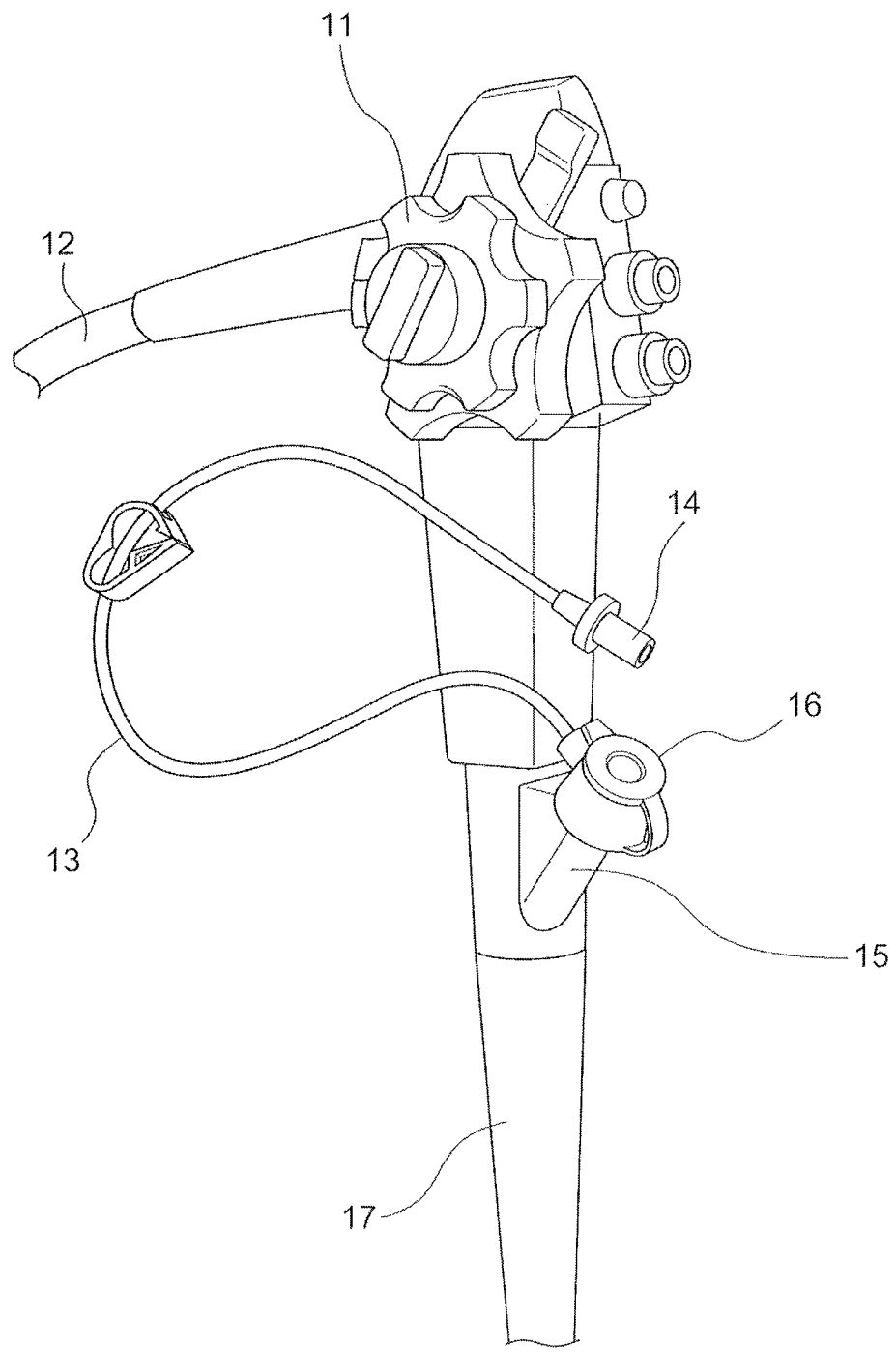
FIG. 1 is a diagram showing a photograph of a proximal part of a medical endoscope.

The viscoelastic composition of the present invention comprises a thickening substance and water.

The viscoelastic composition of the present invention may be prepared by combining one or more kinds of thickening substances having a property of increasing viscosity when dispersed in water. Examples of such thickening substances include alcohols such as methanol, ethanol, 2-propanol, 1,4-butanediol, 1,3-butylene glycol, propylene glycol, glycerin catechin, glucose, fructose, galactose, sucrose, lactose, maltose, trehalose, xylitol, sorbitol, mannitol, glucosamine, and galactosamine; polysaccharides such as *Aureobasidium* culture solution, flaxseed gum, gum Arabic, arabinogalactan, alginic acid and salts thereof, propylene glycol alginate ester, welan gum, *Cassia* gum, gum ghatti, curdlan, carrageenan, karaya gum, xanthan gum, guar gum, guar gum enzymolysis products, *psyllium* seed gum, *Artemisia sphaerocephala* seed gum, gellan gum, succinoglycan, tamarind gum, tara gum, dextran, tragacanth gum, furcellaran, funoran, pullulan, pectin, macrophomopsis gum, Rhamsan gum, levan, locust bean gum, starch grafted acrylate, acetylated distarch adipate, acetylated oxidized starch, acetylated distarch phosphate, starch sodium octenylsuccinate, carboxymethyl cellulose and salts thereof, carboxymethyl ethyl cellulose, starch acetate, oxidized starch, sodium starch glycolate, hydroxypropyl distarch phosphate, hydroxypropyl cellulose, hydroxypropyl starch, hydroxypropyl methyl cellulose, hydroxymethyl cellulose, hydroxyethyl methyl cellulose, hydroxyethyl cellulose, ethyl cellulose, methyl cellulose, cellulose, distarch phosphate, monostarch phosphate, phosphateddistarch phosphate, fucoidan, diutan gum, glucomannan, hyaluronic acid and salts thereof, keratan sulfate, heparin, chondroitin sulfate, dermatan sulfate, scleroglucan, schizophyllan, okra extracts, Krantz aloe extracts, sesbania gum, agarose, agaropectin, amylose, amylopectin, pregelatinized starch, inulin, levan graminan, agar, hydroxypropyl methylcellulose stearoxy ether, sodium starch glycolate, dextran, dextrin, croscarmellose sodium, glucuronoxylan, and arabinoxylan; proteins such as gelatin, hydrolyzed gelatin, and collagen; polyamino acids such as polyglutamic acid, polylysine, and polyaspartic acid; hydrophilic polymers such as a carboxyvinyl polymer, polyacrylic acid and salts thereof, a partially neutralized polyacrylic acid, polyvinyl alcohol, a polyvinyl alcohol-polyethylene glycol graft copolymer, polyethylene glycol, polypropylene glycol, and polybutylene glycol; and metal salts such as calcium chloride, aluminum hydroxide, magnesium chloride, and copper sulfate.

The water used in the viscoelastic composition of the present invention is not particularly limited, but preferably is softened water, pure water, deionized water, distilled water, or a physiological aqueous solution such as physiological saline, Ringer's solution, or acetated Ringer's solution.

The viscoelastic composition of the present invention may comprise one or more additives such as a preservative or an antiseptic agent.

The problem of the present invention is to provide a viscoelastic composition having excellent operability and capable of securing a satisfactory field of view, and desirably, to provide a viscoelastic composition that also makes it possible to assist a simplified hemostasis treatment. Among these problems, the obstruction of the field of view of an endoscope is considered to be caused by liquid such as blood, intestinal juice or bile, or a semi-solid material such as food residue or excrement that: 1) accumulates inside a canal lumen; 2) mixes with water and thereby impairing transparency; and/or 3) flows or diffuses by water conveyance. In order to secure the satisfactory field of view, a transparent composition having viscoelasticity that is different from that of liquid such as blood, intestinal juice or bile, or a semi-solid material such as excrement may be injected into the lumen, thereby physically pushing aside and removing these materials and then securing a space. Also, the transparent composition is not easily mixed with the liquid such as blood, intestinal juice or bile, or the semi-solid material such as excrement, and thus may suppress flowing or diffusion of the liquid. On the other hand, the problem of having excellent operability means that the viscoelastic composition can pass through a forceps opening of an endoscope without excessive resistance. The problem of making it possible to assist a simplified hemostasis treatment means that a hemorrhage site can be recognized in the presence of the viscoelastic composition, and an assistance of a hemostasis treatment using a high-frequency current is made possible.

The viscoelastic composition of the present invention preferably has a hardness of 550 N/m$^2$ or less, and more preferably 400 N/m$^2$ or less, a viscosity (25° C.) of 200 to 2,000 mPa·s, and more preferably 500 to 1,500 mPa·s, and a loss tangent of 0.6 or less.

When the hardness is adjusted to the range described above, satisfactory operability is achieved when the composition is injected through the forceps of an endoscope. Furthermore, when the viscosity and loss tangent are adjusted to the ranges described above, improvements are made from the viewpoint of securing the field of view. Further, also from the viewpoint of securing the field of view, the viscoelastic composition may be made transparent.

The viscoelastic composition of the present invention preferably has an electrical conductivity of 250 μS/cm or less, and more preferably 200 μS/cm or less.

When the electrical conductivity is adjusted to the range described above, a viscoelastic composition is obtainable that may be excellent in thermocoagulation hemostasis and is particularly suitable for treatments such as electroscission or electrocoagulation.

The viscoelastic composition of the present invention may be obtained by mixing one or more thickening substances such as those described above with water, and specifically, the viscoelastic composition may be obtained by, e.g., combining two or more kinds of thickening substances, or dissolving one kind of a thickening substance in water or the like, followed by subjecting the resultant to a heating treatment thereby imparting elasticity to the product. When there are bubbles in the viscoelastic composition of the present invention, the field of view is obstructed; therefore, it is preferable that the viscoelastic composition substantially includes no bubbles.

A method for securing the field of view of an endoscope of the present invention comprises feeding the viscoelastic composition of the present invention from a proximal part of the endoscope, through a channel, into a distal part of the endoscope.

FIG. 1 is a diagram showing a photograph of a proximal part of a medical endoscope as a representative example of endoscopes. The proximal part includes a dial 11 for performing an angle manipulation; a scope connector unit 12 for transmitting light from a light source apparatus and transmitting the information of images to an electronic endoscope processor; and a forceps opening 15 through which a treatment tool such as forceps is inserted and conveyed to the distal part 1. A channel that connects through from the forceps opening to the distal part, a water conveying duct for washing the lens in the distal part with water, an optical system and the like are provided inside an endoscope flexible tube 17. A forceps lid 16 is provided at the forceps opening 15 of the medical endoscope illustrated in FIG. 1. One end of a tube 13 is connected to the forceps lid 16, and the other end of the tube is connected to a connector 14 which is to be mounted to a syringe or the like. The forceps lid 16 is provided inside with a valve body, one end of the tube 13 is opened toward a wall surface of the valve body inside the forceps lid 16, the wall surface being on the side of the forceps opening 15, so that even when a treatment tool such as forceps is inserted, the liquid that has been injected through the tube is prevented from flowing out due to the valve body (see, for example, JP 2014-155677 A).

EXAMPLES

Reference Example

Figure 2A:
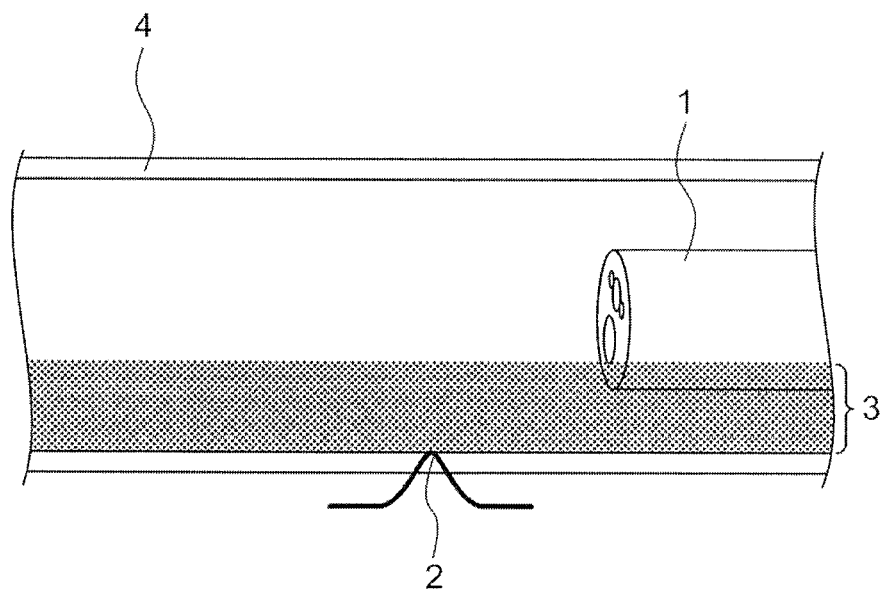
FIG. 2A is a conceptual diagram illustrating the state of the interior of an alimentary canal that has hemorrhaged.
Figure 2B:
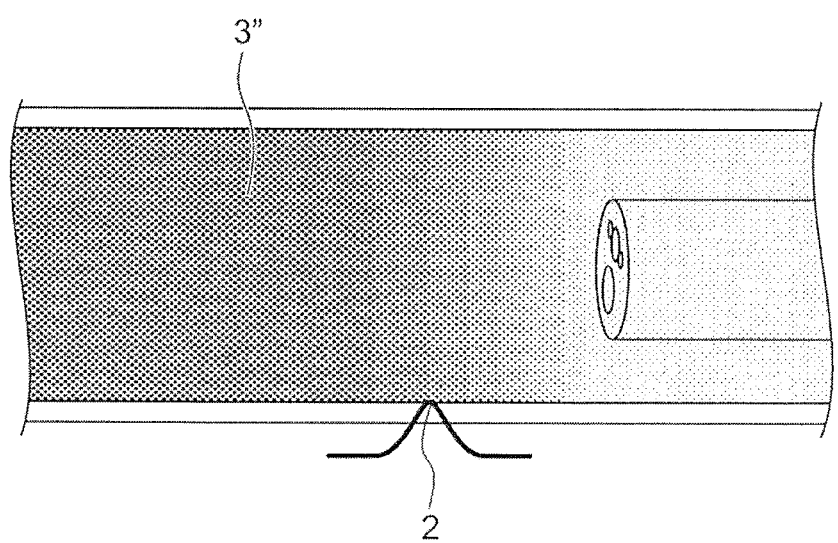
FIG. 2B is a conceptual diagram illustrating the state in which water has been injected into the hemorrhaged alimentary canal.
Figure 9:
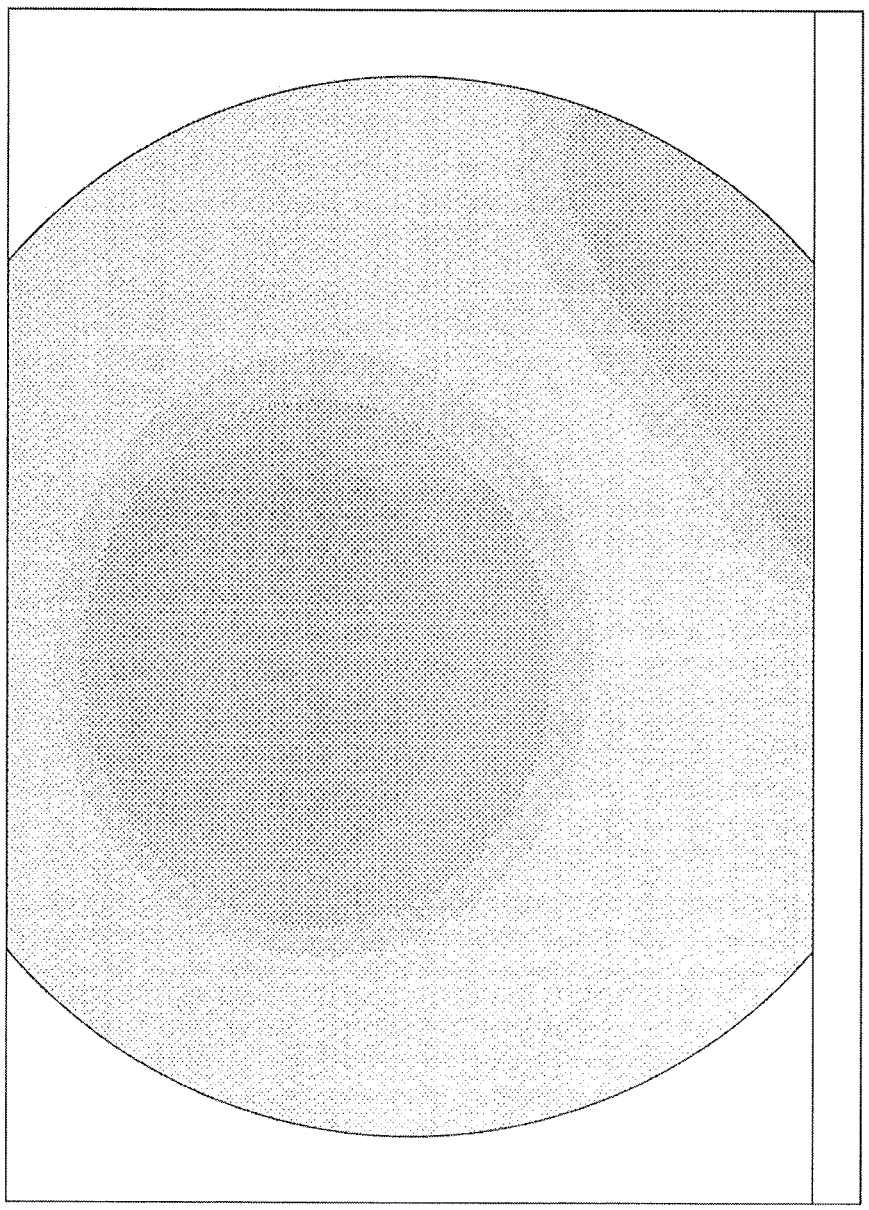
FIG. 9 is a diagram illustrating an example of camera images obtained when water is injected from the forceps of an endoscope.

An endoscope may be inserted into an alimentary canal such as the rectum, thereby making it possible to observe the inside of the alimentary canal using the endoscope. When hemorrhage occurs in an alimentary canal 4, blood 3 accumulates inside the alimentary canal, and a hemorrhage site 2 cannot be observed (FIG. 2A). In such circumstances, the accumulated blood was attempted to be washed away with water by filling a syringe with tap water and injecting the water by the syringe through a tube 13, a forceps opening 15, and a channel to the opening of the endoscope distal part 1, through which the water was injected into the alimentary canal. However, the injected water was mixed and suspended with the accumulated blood and thus the water became turbid water 3". When the turbid water 3" accumulates inside the alimentary canal, the field of view of the endoscope is obstructed by the turbid water 3", and thus the hemorrhage site 2 cannot be observed. A surgical operation cannot be continued accordingly (FIG. 2B and FIG. 9).

Figure 3A:
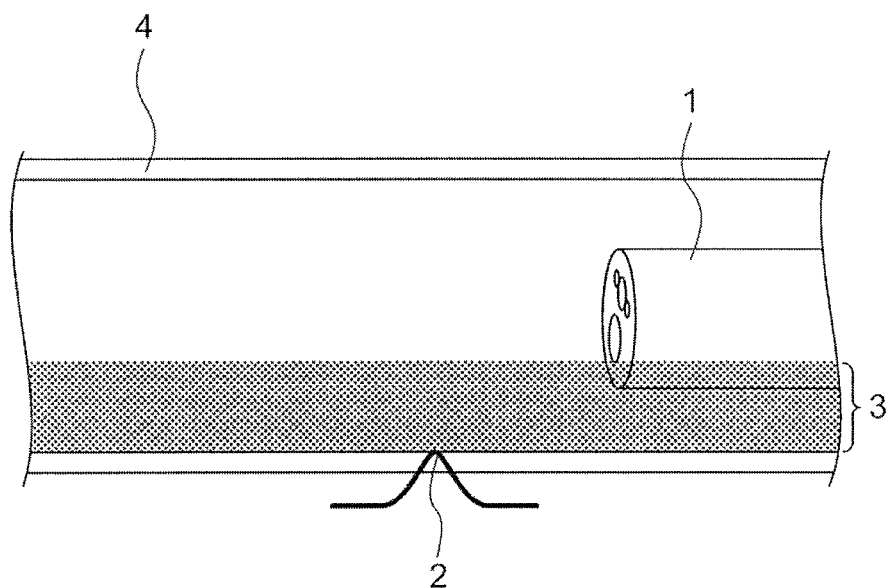
FIG. 3A is a conceptual diagram illustrating the state of the interior of an alimentary canal that has hemorrhaged.
Figure 3B:
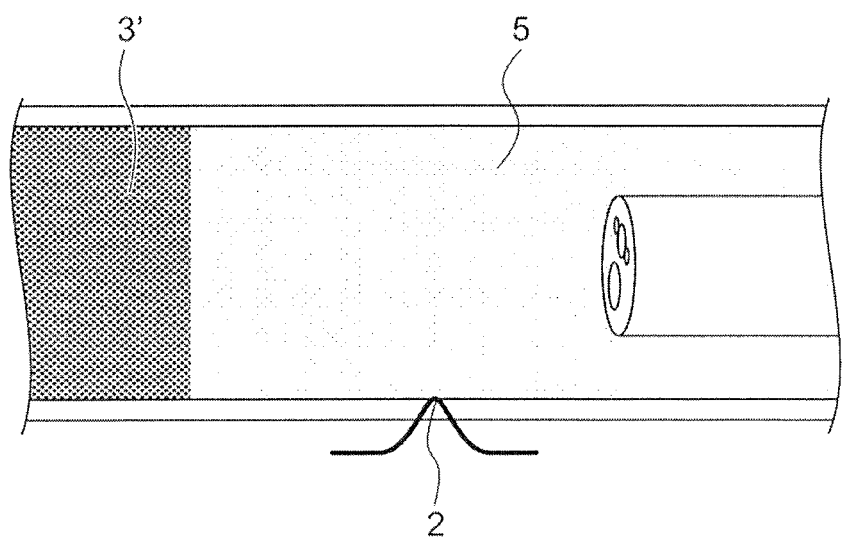
FIG. 3B is a conceptual diagram illustrating the state in which the viscoelastic composition of the present invention has been injected into the hemorrhaged alimentary canal.

In contrast, with regard to the viscoelastic composition of the present invention, when there is a hemorrhage site 2 in an alimentary canal 4, the blood 3 that has accumulated inside the alimentary canal may be pushed aside (blood 3') by injecting the viscoelastic composition from the distal part of the endoscope as illustrated in FIG. 3A and FIG. 3B. The viscoelastic composition of the present invention thus makes it possible to observe the hemorrhage site 2.

Examples and Comparative Examples

In the present Examples or Comparative Examples, the relation between the viscoelastic properties of viscoelastic compositions used for endoscopy and the securement of the field of view and the operability in operating an endoscope was investigated.

Methods for determining the physical properties of viscoelastic compositions and methods for evaluating the viscoelastic compositions from the viewpoint of securing the field of view and from the viewpoint of operability when used for endoscopy are shown below.

(1) Viscosity and Loss Tangent

Viscosity and viscoelasticity are determined using HAAKE RS-6000 (Thermo Fisher Scientific, Inc.). A viscoelastic composition was mounted on a sample stand, and measurements were made using P35 Ti L parallel plates (measurement conditions: temperature 25° C., gap 1.000 mm, stress 1,000 mPa, and frequency 0.5000 Hz). The values obtained after 30 minutes from the initiation of measurement were measured.

(2) Hardness

Hardness is determined using a creepmeter, Model RE2-33005C (YAMADEN Co., Ltd.). A stainless steel Petri dish (outer diameter: 45 mm, inner diameter: 41 mm, external dimension: 18 mm, and internal dimension: 15 mm) was filled with a viscoelastic composition, the height of the viscoelastic composition was aligned with the height of the Petri dish, and the surface of the specimen was made flat. Measurements were made using a plunger (YAMADEN Co., Ltd., shape: disc, model: P-56, remarks: φ20×t 8) (measurement conditions: storage pitch 0.02 sec, measurement distortion rate 66.67%, measurement speed 10 mm/sec, return distance 5.00 mm, sample thickness 15.00 mm, contact surface diameter 20.00 mm, and contact area 0.000 mm$^2$).

(3) Electrical Conductivity

Electrical conductivity was determined using an electrical conductivity meter CM-41X (DKK-TOA CORPORATION) and a CT-57101C cell for low electrical conductivity measurement (measurement conditions: temperature 25° C.).

Figure 4A:
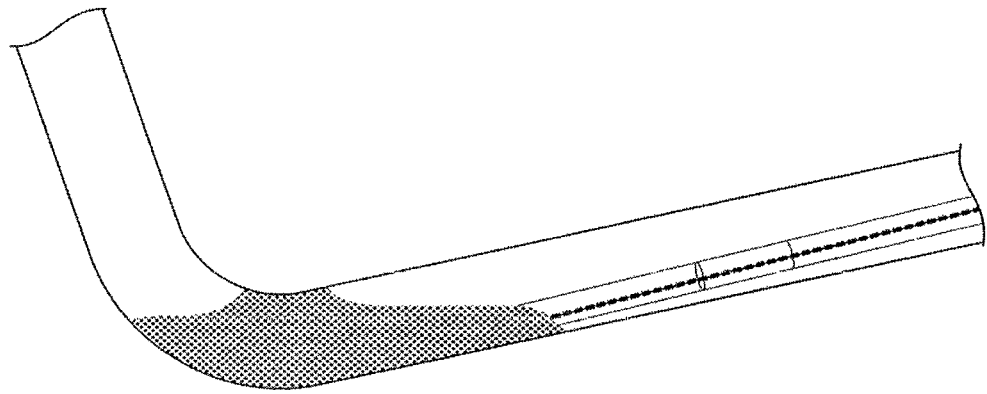
FIG. 4A is a diagram illustrating a method of evaluation from the viewpoint of securing the field of view when a viscoelastic composition is used for endoscopy.
Figure 4B:
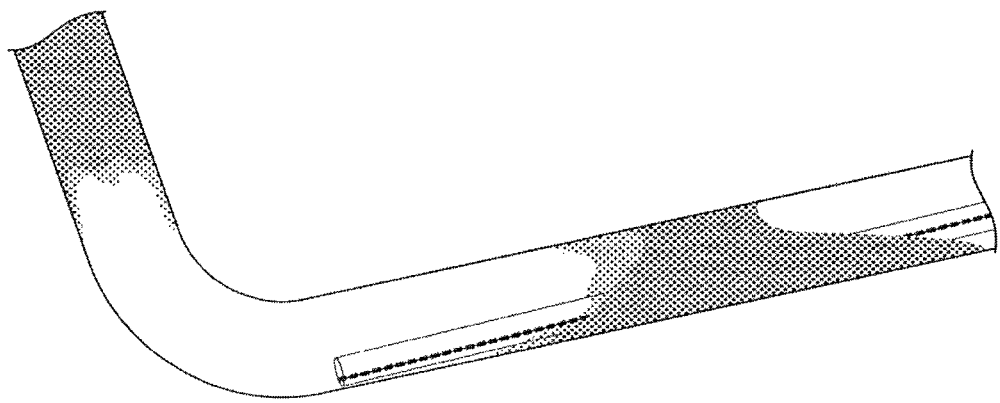
FIG. 4B is a diagram illustrating a method of evaluation from the viewpoint of securing the field of view when the viscoelastic composition is used for endoscopy.
Figure 5A:
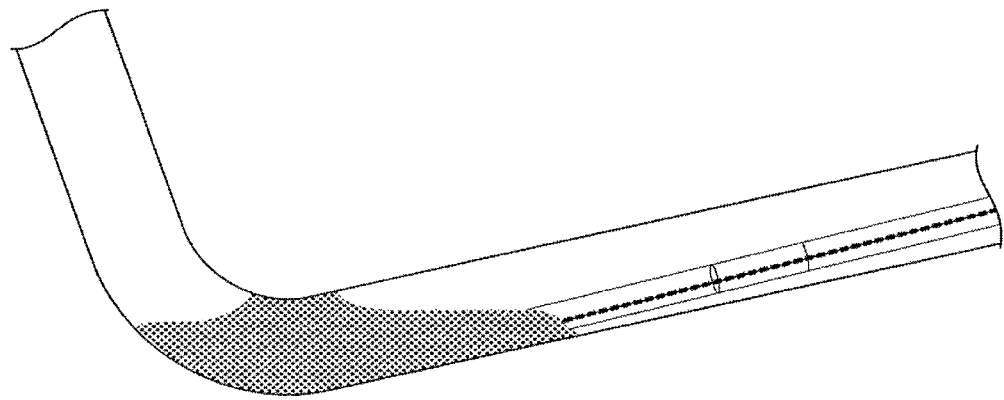
FIG. 5A is a diagram illustrating a method of evaluation from the viewpoint of securing the field of view when a viscoelastic composition is used for endoscopy.
Figure 5B:
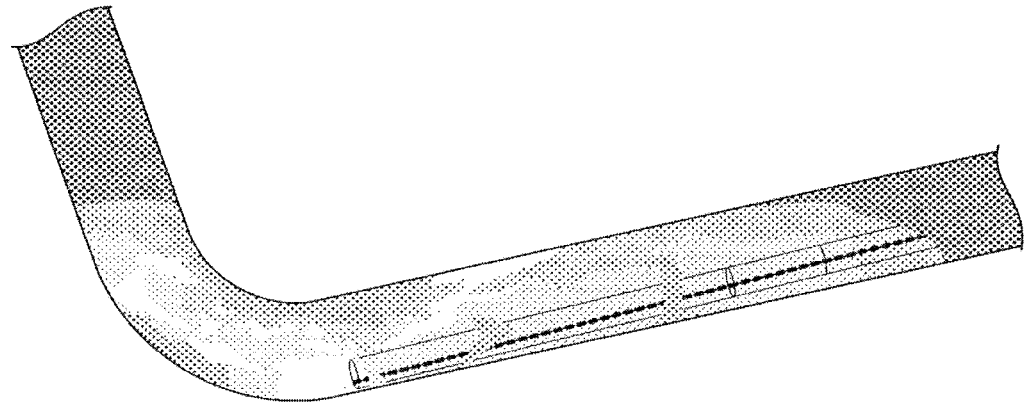
FIG. 5B is a diagram illustrating a method of evaluation from the viewpoint of securing the field of view when the viscoelastic composition is used for endoscopy.

(4) Method for Evaluation in Securing the Field of View 3 mL of a 1% Evans Blue solution (dye solution) was injected into a Dean-Stark trap, and a catheter tube attached with a wire was inserted thereto. In this state, the field of view is obstructed by the dye solution, and the wire at the tip of the tube is not visible (FIG. 4A and FIG. 5A). Each 10 mL of viscous compositions having different loss tangent, hardness and viscosity was injected into the dye solution through the catheter tube (inner diameter: 2.5 to 3 mm, and length: 1.000 mm), and success or failure in securing the field of view was determined by visual inspection. When a certain viscous composition A was injected, a physical space was secured, and the viscous composition A was not easily mixed with the dye solution. In this case, the viscous composition A was considered to exhibit desired viscoelastic properties, and thus was concluded to be "acceptable" as the viscoelastic composition (FIG. 4B). On the other hand, when a viscous composition B different from the viscous composition A was injected, whether a physical space was secured or not was obscure, and the viscous composition B was mixed with the dye solution. In this case, the viscous composition B was not considered to exhibit desired viscoelastic properties, and thus was concluded to be "unacceptable" as the viscoelastic composition (FIG. 5B).

Figure 10:
FIG. 10 is a diagram illustrating an example of camera images obtained when the viscoelastic composition is injected from the forceps of an endoscope.

The results obtained from the evaluation in securing the field of view correspond to the occurrence of differences in providing the field of view as shown in, for example, FIG. 9 and FIG. 10. That is, when an endoscope was inserted to a hemorrhage site and water was injected thereinto, the field of view obtained from a camera was not satisfactory due to turbid water as illustrated in FIG. 9. In contrast, when an endoscope was inserted to a hemorrhage site and a viscoelastic composition exhibiting desired viscoelastic properties was injected thereinto, the hemorrhage site 2 was clearly detected in the field of view obtained from a camera as illustrated in FIG. 10.

(5) Method for Evaluation in Operability

Since a viscoelastic composition used for securing the field of view is injected into an alimentary canal through a forceps opening (inner diameter: 2.8 to 3.8 mm) of an endoscope, the viscoelastic composition may desirably be injected smoothly without any excessive resistance. Each of the viscoelastic compositions having different loss tangent, hardness and viscosity was filled into a 50-mL syringe (JMS Co., Ltd.) and then a catheter tube (inner diameter: 3 mm, and length: 1.000 mm) simulating the inner diameter of a forceps opening of the endoscope was mounted to the tip of the syringe. The passability of the viscoelastic compositions was then subjectively determined. Viscoelastic compositions that passed smoothly or passed with slight resistance at a practically acceptable level were concluded to be "suitable". In contrast, viscoelastic compositions that exhibited too excessive resistance to endure practical uses or exhibited too excessive resistance to pass through the tube were concluded to be "unsuitable".

Figure 6:
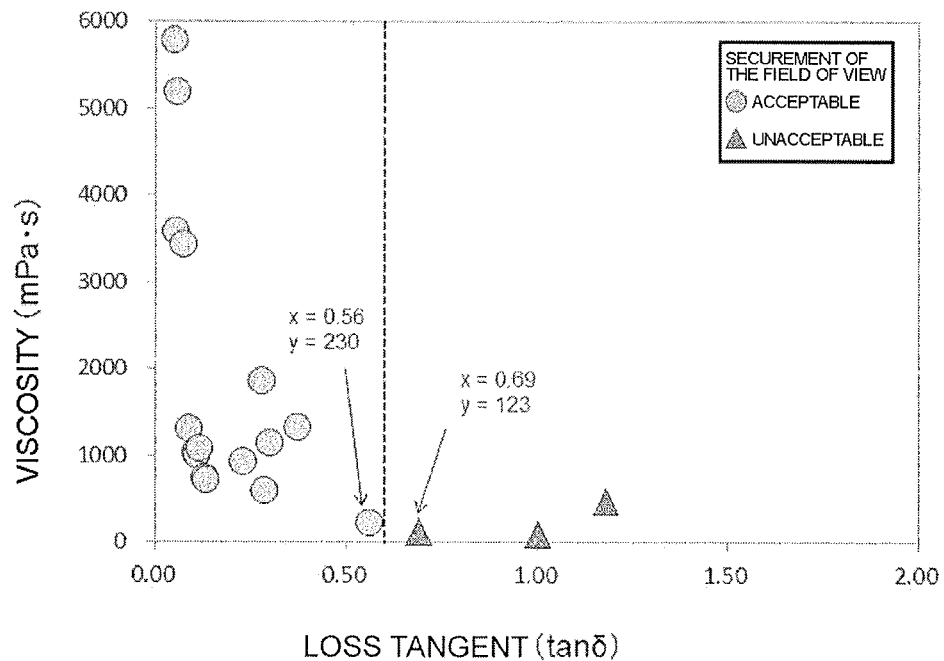
FIG. 6 is a graph showing the relation between the viscosity and loss tangent of the viscoelastic composition and the success or failure in securing the field of view when the viscoelastic composition is used for endoscopy.
Figure 7:
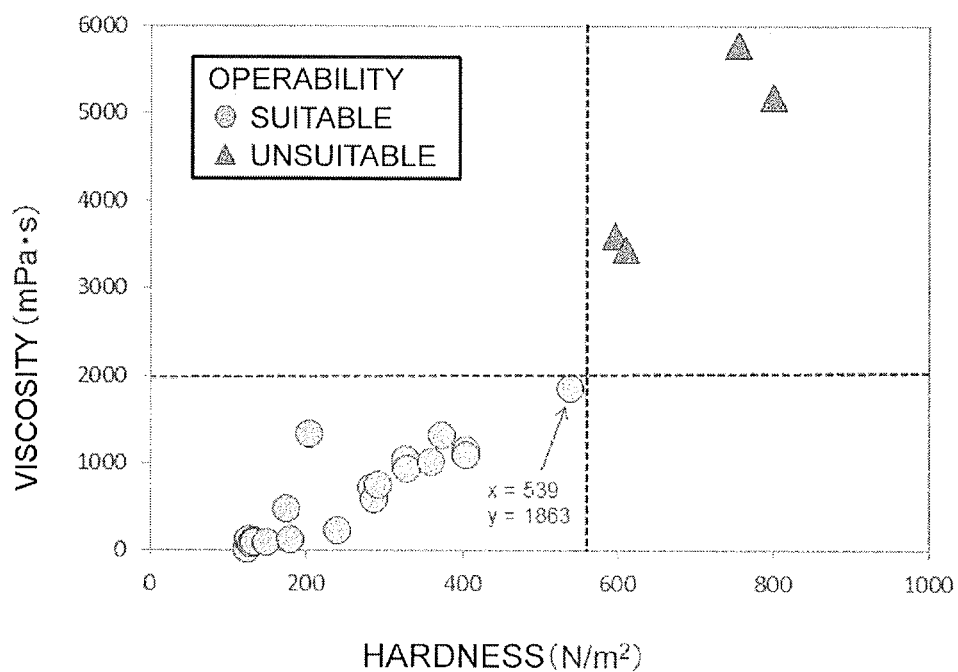
FIG. 7 is a graph showing the relation between the viscosity and hardness of the viscoelastic composition and the suitability or unsuitability in operability when the viscoelastic composition is used for endoscopy.
Figure 8:
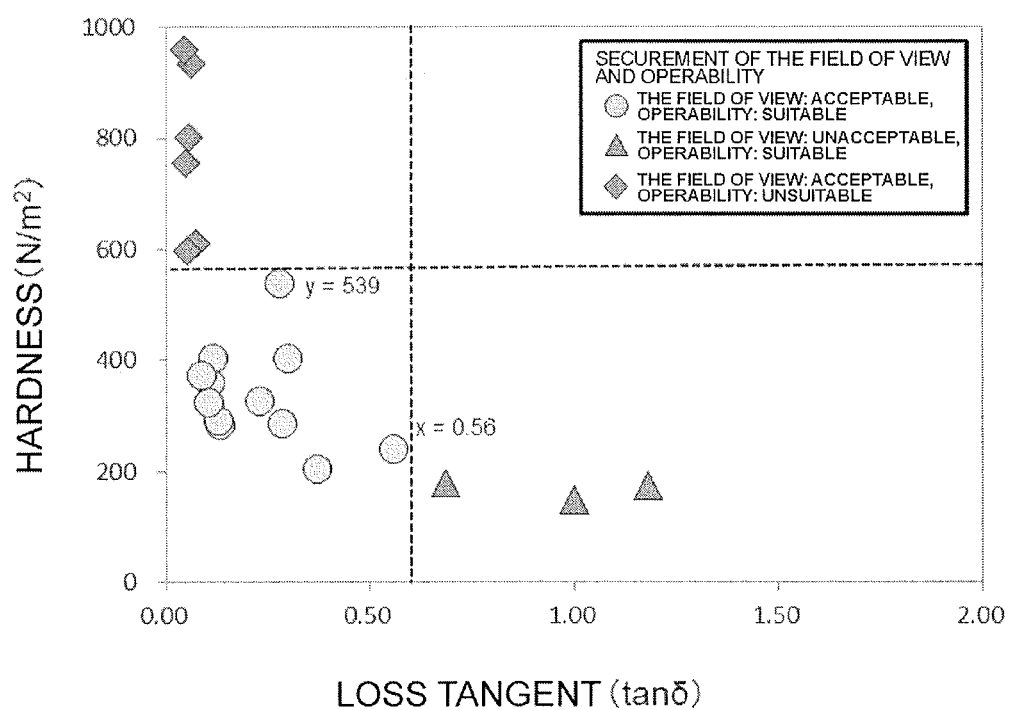
FIG. 8 is a graph showing the relation between the hardness and loss tangent of the viscoelastic composition and the success or failure in securing the field of view and suitability or unsuitability in operability when the viscoelastic composition is used for endoscopy.

Test Example 1: As to the Relation Between Loss Tangent, Hardness, and Viscosity of Viscoelastic Compositions Viscoelastic compositions having different loss tangent, hardness and viscosity were prepared and tested for the securement of the field of view and operability, and then the relation thereof with various physical properties was evaluated. All the loss tangents of the viscoelastic compositions that were concluded to be "acceptable" in securing the field of view were about 0.6 or less, whereas all the viscoelastic compositions having a higher loss tangent were concluded to be "unacceptable" (FIG. 6). The viscoelastic compositions that were concluded to be "suitable" in operability had a hardness of about 550 N/m$^2$ or less and a viscosity of about 2,000 mPa·s or less, whereas all the viscoelastic compositions having a higher hardness or viscosity were concluded to be "unsuitable" (FIG. 7). The loss tangent and hardness of the viscoelastic compositions that satisfied both the "acceptable" in securing the field of view and the "suitable" in operability are the same as those described above (FIG. 8). It was found from these experimental examples that a viscoelastic composition having a loss tangent of 0.6 or less, a hardness of 550 N/cm$^2$ or less, and a viscosity of 200 to 2,000 mPa·s is preferable in order to achieve the excellent properties in securing the field of view and operability in endoscopic treatments.

Test Example 2: As to the Electrical Conductivity of Viscoelastic Compositions

There are three methods for endoscopic hemostasis; a method based on thermocoagulation using a high frequency-current, a method using a clip, and a method using one or more medicines. In a thermocoagulation method, a high-frequency current is passed through a hemorrhage site, and tissues are coagulated and stanched by means of the heat generated concentratedly at the hemorrhage site. In this instance, generally, if a solution or a substance having high electrical conductivity exists in the vicinity of the hemorrhage site, the high-frequency current would leak, and satisfactory thermocoagulation could not be achieved.

Based on the knowledge, treatments and evaluation were performed according to the following procedure.

Figure 11:
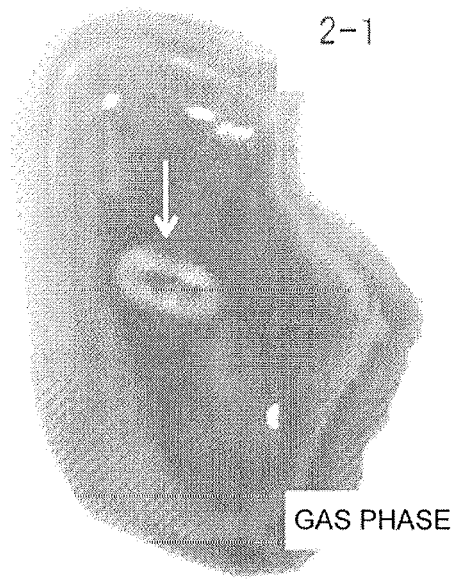
FIG. 11 is a diagram illustrating the result of a thermocoagulation treatment using a high-frequency current, the treatment simulating a treatment with an endoscope.
Figure 12:
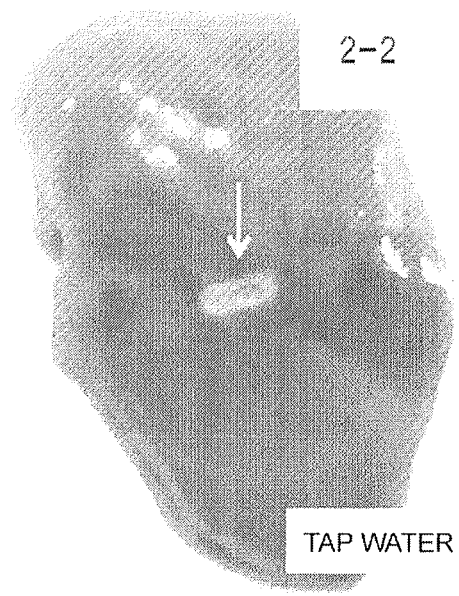
FIG. 12 is a diagram illustrating the result of the thermocoagulation treatment using a high-frequency current, the treatment simulating the treatment with the endoscope.
Figure 13:
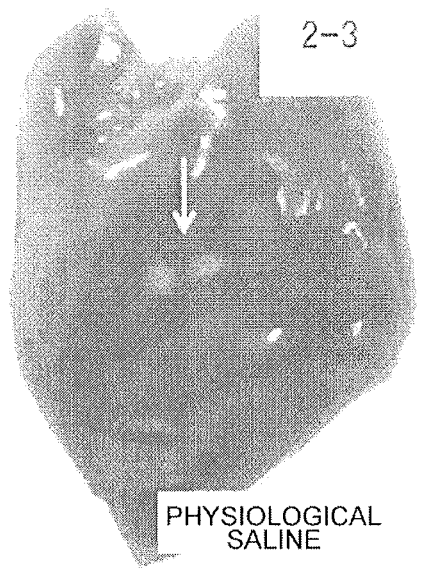
FIG. 13 is a diagram illustrating the result of the thermocoagulation treatment using a high-frequency current, the treatment simulating the treatment with the endoscope.
Figure 14:
FIG. 14 is a diagram illustrating the result of the thermocoagulation treatment using a high-frequency current, the treatment simulating the treatment with the endoscope.
Figure 15:
FIG. 15 is a diagram illustrating the result of the thermocoagulation treatment using a high-frequency current, the treatment simulating the treatment with the endoscope.
Figure 16:
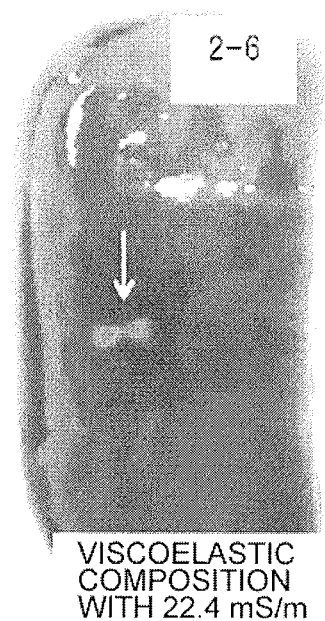
FIG. 16 is a diagram illustrating the result of a thermocoagulation treatment using a high-frequency current, the treatment simulating the treatment with the endoscope.
Figure 17:
FIG. 17 is a diagram illustrating the result of a thermocoagulation treatment using a high-frequency current, the treatment simulating the treatment with the endoscope.

A small tube (diameter: about 1.5 cm) was compressively bonded to the surface of the liver of a rat, and the interior of the tube was filled with physiological saline, distilled water, or viscoelastic compositions that had been prepared to have different electrical conductivities. The tip of a unipolar electrode (Edge-coated blade electrode E1450X) was softly pressed against the liver surface, and electricity was passed for 2 seconds in the coagulation mode (SURGISTAT II, Covidien Japan, Inc., set to a coagulation output of 20). Satisfactory thermocoagulation was observed in a gas phase (FIG. 11) and in tap water having a low electrical conductivity (FIG. 12); however, unsatisfactory thermocoagulation was observed in physiological saline having a high electrical conductivity (FIG. 13). Further, satisfactory thermocoagulation was observed in viscoelastic compositions having an electrical conductivity of 12.8 mS/m (128 μS/cm) or less (FIG. 14 and FIG. 15), and thermocoagulation to the extent that it had no problem for practical uses was observed in a viscoelastic composition having an electrical conductivity of 25 mS/m (250 μS/cm) or less, for example, 22.4 mS/m (224 μS/cm) or less (FIG. 16). However, unsatisfactory thermocoagulation was observed in a viscoelastic composition having a high electrical conductivity, for example, 60.8 mS/m (608 μS/cm) (FIG. 17). It was found from these experimental examples that a viscoelastic composition which is excellent in securing the field of view and operability in endoscopic treatments should have an electrical conductivity of preferably 25 mS/m or less, and more preferably 20 mS/m or less in consideration of thermocoagulation hemostasis using a high-frequency current. The results are also shown in the following Table 1.

TABLE 1

Electrical conductivity of viscoelastic compositions (thermocoagulation)

| Material | Electrical conductivity(mS/m) | Thermo-coagulation* |
|---|---|---|
| 2-1 Gas phase | — | E |
| 2-2 Tap water | 10 | E |
| 2-3 Physiological saline | 1600 | NG |
| 2-4 Viscoelastic composition | 1.8 | E |
| 2-5 Viscoelastic composition | 12.8 | E |
| 2-6 Viscoelastic composition | 22.4 | G |
| 2-7 Viscoelastic composition | 60.8 | NG |

*E: Excellent (satisfactory thermocoagulation was observed)
G: Good (thermocoagulation was observed)
NG: Not Good (thermocoagulation was insufficient)

In the following Table 2, viscoelastic compositions that were concluded to be "suitable" in operability in endoscopic treatments and were capable of realizing thermocoagulation using a high-frequency current are shown, and about the respective viscoelastic compositions, success or failure in securing the field of view is also shown.

REFERENCE SIGNS LIST

1 Endoscope distal portion
2 Hemorrhage site
3, 3' Blood
3" Turbid water
11 Dial
12 Scope connector unit
13 Tube
14 Connector
15 Forceps opening
16 Forceps lid
17 Endoscope flexible tube

What is claimed is:

1. A method for securing the field of view of an endoscope, the method comprising feeding a viscoelastic composition comprising a thickening substance and water and having a loss tangent of 0.6 or less from a proximal part of the endoscope, through a channel, into a distal part of the endoscope so as to physically push aside or remove dark-colored liquid or a semi-solid material accumulated inside a canal, thereby securing the field of view of the endoscope.

2. The method according to claim 1, wherein the endoscope is a medical endoscope.

3. The method of claim 1, wherein the viscoelastic composition has a hardness of 550 N/m$^2$ or less and a viscosity at 25° C. of 200 to 2,000 mPa·s.

4. The method according to claim 3, wherein the endoscope is a medical endoscope.

5. The method of claim 3, wherein the viscoelastic composition has an electrical conductivity of 250 pS/cm or less.

6. The method according to claim 5, wherein the endoscope is a medical endoscope.

7. The method of claim 1, wherein the viscoelastic composition has an electrical conductivity of 250 pS/cm or less.

8. The method according to claim 7, wherein the endoscope is a medical endoscope.

9. The method according to claim 1, wherein the thickening substance comprises a polysaccharide or a hydrophilic polymer.

10. The method according to claim 3, wherein the thickening substance comprises a polysaccharide or a hydrophilic polymer.

11. The method according to claim 5, wherein the thickening substance comprises a polysaccharide or a hydrophilic polymer.

TABLE 2

| Viscoelastic composition | Concentration (wt %) | Ratio | Viscosity (mPa · s) | Loss tangent | Hardness (N/m$^2$) | Securement of the field of view | Operability |
|---|---|---|---|---|---|---|---|
| Xanthan gum:Locust bean gum | 0.08 | 4:6 | 1012 | 0.11 | 360 | Acceptable | Suitable |
|  | 0.08 | 8:2 | 123 | 0.69 | 180 | Unacceptable | Suitable |
|  | 0.12 | 8:2 | 230 | 0.56 | 241 | Acceptable | Suitable |
|  | 0.20 | 2:8 | 3597 | 0.58 | 596 | Acceptable | Unsuitable |
| Tamarind gum:Sucrose | 11.0 | 1:10 | 97 | 104.7 | 134 | Unacceptable | Suitable |
| Tamarind gum:D-mannitol | 11.0 | 1:10 | 110 | 9.36 | 134 | Unacceptable | Suitable |
| Tamarind gum:Glycerin | 11.0 | 1:20 | 89 | 69.83 | 131 | Unacceptable | Suitable |
| Carrageenan:Locust bean gum | 0.10 | 6:4 | 13 | 4.03 | 125 | Unacceptable | Suitable |
| Hypromellose | 8.00 | — | 581 | 140 | 153 | Unacceptable | Suitable |
| Sodium carboxymethyl cellulose | 1.50 | — | 1112 | 1.34 | 215 | Unacceptable | Suitable |
| Xanthan gum:Tara gum | 0.40 | 7:3 | 1863 | 0.28 | 539 | Acceptable | Suitable |
|  | 0.10 | 7:3 | 101 | 1.00 | 150 | Unacceptable | Suitable |
| Sodium alginate/Calcium chloride | 2.73/0.16 | — | 1858 | 0.43 | 395 | Acceptable | Suitable |

12. The method according to claim 7, wherein the thickening substance comprises a polysaccharide or a hydrophilic polymer.

\* \* \* \* \*

UNITED STATES PATENT AND TRADEMARK OFFICE
CERTIFICATE OF CORRECTION

PATENT NO. : 11,458,229 B2
APPLICATION NO. : 15/764243
DATED : October 4, 2022
INVENTOR(S) : Tomonori Yano et al.

It is certified that error appears in the above-identified patent and that said Letters Patent is hereby corrected as shown below:

In the Claims

Claim 5, Column 10 Line 30-31:
The method of claim 3, wherein the viscoelastic composition has an electrical conductivity of 250 pS/cm or less.
Should be:
The method of claim 3, wherein the viscoelastic composition has an electrical conductivity of 250 µS/cm or less.

Claim 7, Column 10 Line 35-36:
The method of claim 1, wherein the viscoelastic composition has an electrical conductivity of 250 pS/cm or less.
Should be:
The method of claim 1, wherein the viscoelastic composition has an electrical conductivity of 250 µS/cm or less.

Signed and Sealed this
Sixth Day of June, 2023

Katherine Kelly Vidal
*Director of the United States Patent and Trademark Office*